United States Patent [19]

Grill et al.

[11] Patent Number: 4,778,925

[45] Date of Patent: Oct. 18, 1988

[54] NEW BENZOIC ACID DERIVATIVES, AS WELL AS PROCESSES FOR THEIR PRODUCTION AND THEIR USE AS PHARMACEUTICALS

[75] Inventors: Helmut Grill, Vaterstetten; Friedemann Reiter, Putzbrunn; Michael Schliack, Munich; Roland Löser, Feldafing; Klaus Seibel, Grafelfing, all of Fed. Rep. of Germany

[73] Assignee: Klinge Pharma GmbH, Munich, Fed. Rep. of Germany

[21] Appl. No.: 52,917

[22] Filed: May 22, 1987

[51] Int. Cl.$^4$ ............................................. C07C 101/34
[52] U.S. Cl. ........................................ 562/450; 562/459; 562/473
[58] Field of Search ................ 502/459, 444, 475, 450; 560/38, 39, 51, 64; 514/563, 568

[56] References Cited

U.S. PATENT DOCUMENTS

| | | | |
|---|---|---|---|
| 4,067,892 | 1/1978 | Thorne et al. | 260/410 |
| 4,073,935 | 2/1978 | Grill et al. | 424/308 |
| 4,154,850 | 5/1979 | Morgan et al. | 424/308 |
| 4,189,594 | 2/1980 | Grill et al. | 560/53 |
| 4,582,857 | 4/1986 | Grill et al. | 514/563 |

FOREIGN PATENT DOCUMENTS

| | | |
|---|---|---|
| 2735856 | 2/1979 | Fed. Rep. of Germany ........ 560/53 |
| 2460689 | 6/1980 | Fed. Rep. of Germany ...... 514/413 |
| 3326164 | 1/1985 | Fed. Rep. of Germany ...... 514/563 |

Primary Examiner—James H. Reamer
Attorney, Agent, or Firm—Burns, Doane, Swecker & Mathis

[57] ABSTRACT

Para substituted benzoic acid derivatives of general formula (1)

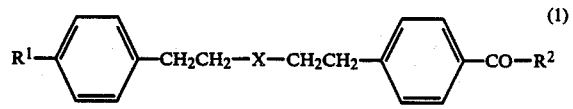

and their physiologically compatible salts, where $R^1$ may be H, isopropyl, t-butyl p0 X may be

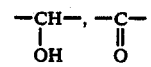

and
$R^2$ may be —OH, —OR′, where R′ is a linear or branched, saturated or unsaturated $C_1$ to $C_3$ alkylmoiety, or a —NHCH$_2$COOH— group, have hypolipedemic activity. They may be obtained by known methods either from the corresponding unsaturated ketones or from saturated hydroxycompounds, where the esterified benzoic acid moiety may be saponified or converted to a carboxymethylamide.

2 Claims, No Drawings

NEW BENZOIC ACID DERIVATIVES, AS WELL AS PROCESSES FOR THEIR PRODUCTION AND THEIR USE AS PHARMACEUTICALS

BACKGROUND OF THE INVENTION

Numerous agents have been introduced for the treatment of disturbances of lipid metabolism. CLOFIBRAT was one of the first representatives of the group of aryloxy-isoalkane acids. Because of its weak activity a series of derivatives, for example ETOFIBRAT or ETOFYLLINCLOFIBRAT as well as structural analogs such as BFZAFIBRAT, FENOFIBRAT or GEMFIBROZIL were developed. However, they resembled CLOFIBRAT with respect to undesirable activities, which led to the conclusion of a similar mechanism of action. Known side effects include gastrointestinal reactions, loss of appetite, nausea, allergic reactions, myositis, myalgia, and impotence as well as increase in serum creatinine, serum urea and the lithogenic index; a lowering of alkaline phosphatase, an increase in creatinine phosphokinase and stimulation of peroxisome formation.

Circumvention of these deficiencies appears to be possible only through the discovery of new agents, based on clearly modified structures which may be expected to lead to changes in biological properties.

SUMMARY OF THE INVENTION

Compounds comprising benzoic acid derivatives of formula (1)

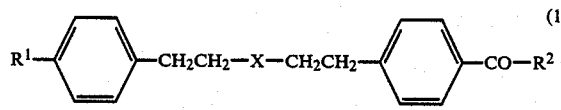

and their physiologically compatible salts, where
$R^1$ = H, isopropyl, or t-butyl
X =

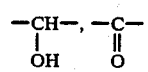

and
$R^2$ = —OH, or —OR', where $R^1$ may be a straight chain, branched, saturated or unsaturated $C_1$ to $C_3$-alkylmoiety, or a —NHCH$_2$COOH— group.

Surprisingly, it has now been found that benzoic acid derivatives of Formula (1) as indicated in claim 1 are clearly superior in hypolipemic activity to BEZAFIBRAT. This involves para substituted phenylpentanol—or phenylpentanonebenzoic acids which belong to a not previously described series of structures.

Benzoic acid derivatives with ether substituents in the para position, with hypolipemic properties, are known. Among these compounds are ethers of glycerin (DE-PS No. 24 60 689), of 1,3-dihydroxyacetone (DE-OS No. 27 35 856) and other alcohols (DE-OS No. 33 26 164; U.S. Pat. No. 4,067,892; U.S. Pat. No. 4,154,850). Because of the ether function, alterations in biological properties must be expected.

The preparation of these new hypolipidemically active compounds can be carried out by known procedures, using the process set forth below.

The starting materials needed for the synthesis of the compounds according to this invention can be prepared by the following procedures.

Condensation of acetone with aldehydes of the general formula (7)

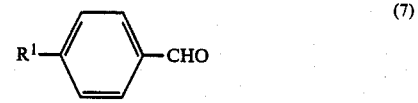

where $R^1$ is hydrogen, isopropyl, or t-butyl benzalacetonides of general formula (8)

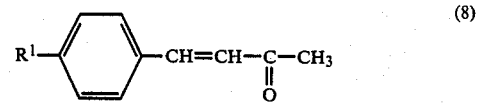

Reaction with 4-formylbenzoic acid alkylester of general formula (9)

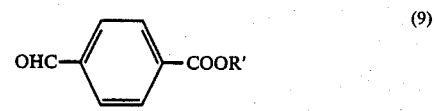

where R' is a straight chain, branched, saturated or unsaturated $C_1$ to $C_3$-alkyl moiety, or a —NHCH$_2$COOH group, leads to 1,4-pentadienones of general formula (2)

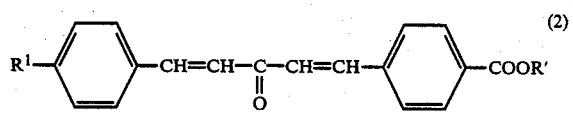

which can be selectively reduced with benzylalcohol in the presence of Tris(triphenylphosphin)ruthenium-II-chloride to compounds of general formula (3), according to this invention

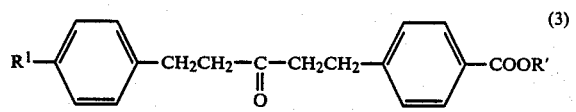

By alkaline saponification followed by acidification with mineral acid one obtains the compounds of general formula (10), according to the invention.

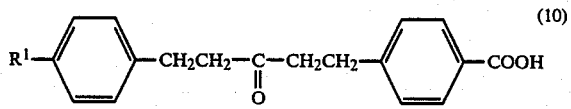

Compounds of general formula (3) can be reduced in the cold with sodium borohydride to compounds of the invention with general formula (4)

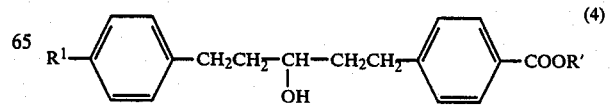

and converted, by alkaline saponification followed by acidification with mineral acid, to the acids of the invention with general formula (11).

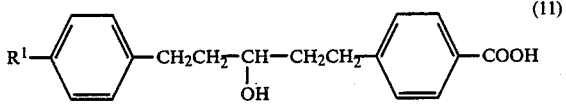

Reaction with acetylchloride yields compounds with general formula (12)

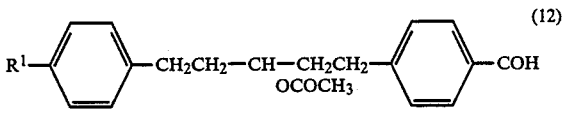

which can be converted to acid chlorides with general formula (13) by reaction with thionylchloride

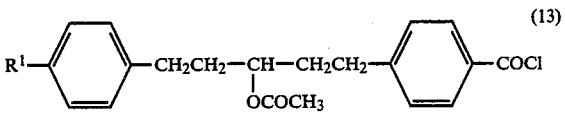

Compounds according to this invention with general formula (14) are obtained by reaction with sodium glycinate followed by alkaline saponification, and acidification with mineral acid.

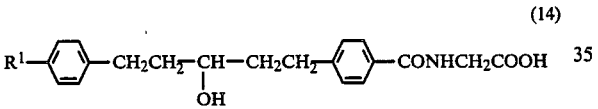

Compounds with general formulas (4), (11), and (14) are converted to compounds according to this invention with general formula (15) by selective oxidation with dimethylsulfoxide.

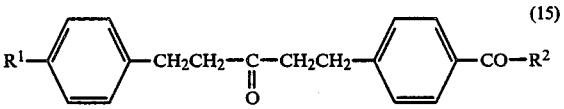

where $R^1$ has the meaning indicated above and $R^2$ is —OH or —OR'.

In order to further illustrate the present invention and the advantages thereof, the following specific examples are given, it being understood that these examples are intended only to be illustrative without serving as a limitation on the scope of the present invention.

EXAMPLES

The superiority of the claimed compounds over BEZAFIBRAT, which was introduced to therapy a long time ago, can clearly be demonstrated by the lipid lowering activity.

Lipid lowering activity was evaluated in normolipemic, male Wistar rats, 10 per group, weighing between 200 and 220 grams.

The tests were carried out after three weeks of retraining the animals to new feeding habits. Controlled feeding took place daily from 10:00 to 12.00 o'clock. Administration of test materials took place at 11:00 o'clock.

The test compounds were taken up in an aqueous solution of 0.25% agar and 0.84% sodium chloride and administered orally. Blood samples were removed from the animals after administration of $3 \times 100$ mg/kg over a three day time period.

Cholesterol and triglyceride determinations were carried out with a Hoffman-LaRoche "Cobas Bio" centrifugal analyzer.

Methods:

(a) Cholesterol determination

CHOD-PAP-method; colorimetric enzyme assay according to J. Siedel et al (J. Clin. Chem. Clin. Biochem. 19,838 (1981))

(b) Triglyceride determination

Enzymatic cleavage of triglycerides with special lipases followed by enzymatic determination of the liberated glycerin. (H. U. Bergmeyer, "Methods of enzymatic analysis", 3rd edition, Vol II, Verlag Chemie, Weinheim, 1974, page 1878).

TABLE 1

Percent change in total cholesterol (TC) and triglyceride (TG) levels in rat serum after oral administration of test materials

| | % Change | |
|---|---|---|
| Compound Number | TC $X \pm S_x$ | TG $X \pm S_x$ |
| comparison compound BEZAFIBRAT | $-22.3 \pm 15.8$ | $+6.1 \pm 9.9$ |
| 2 | $-29.0 \pm 10.8$ | $-42.6 \pm 12.8$ |
| 3 | $-26.1 \pm 17.2$ | $-21.9 \pm 11.5$ |
| 4 | $-26.3 \pm 13.9$ | $-42.0 \pm 7.0$ |
| 5 | $-17.6 \pm 15.0$ | $-37.4 \pm 12.7$ |
| 6 | $-9.1 \pm 5.6$ | $-25.3 \pm 20.4$ |
| 7 | $-35.1 \pm 9.7$ | $-31.3 \pm 13.0$ |
| 8 | $-23.1 \pm 13.1$ | $-38.5 \pm 13.0$ |
| 9 | $-35.6 \pm 20.9$ | $-64.6 \pm 15.8$ |
| 10 | $-15.4 \pm 10.7$ | $-31.3 \pm 25.6$ |
| 11 | $-26.1 \pm 7.2$ | $-35.4 \pm 14.7$ |
| 13 | $-6.9 \pm 21.7$ | $-15.7 \pm 14.8$ |
| 14 | $-24.8 \pm 18.4$ | $-45.4 \pm 12.4$ |
| 15 | $-28.0 \pm 7.7$ | $-20.1 \pm 7.1$ |

For therapeutic use as hypolipemic agents the new compounds with the general formula (1), and their salts, are preferably administered orally. Generally the daily oral dose for adults is 0.1 to 1 gram.

For oral administration the agents can be compounded in the usual galenic fashion. Adjuvants such as lactose, sugars, mannitol, potato—or cornstarch, cellulose derivatives or gelatin are suitable as pharmaceutical carriers, occasionally with addition of lubricants such as magnesium- or calcium stearate, as well as polyethylene glycols.

Preferred dosage forms are hard gelatin "steck" capsules as well as closed soft gelatin capsules. The liberation of the claimed compounds can be accelerated or slowed according to the pharmaceutical compounding.

The "steck" capsules can contain pure agent, or possibly a small addition of a lubricant. When compounded into soft gelatin capsules the pure agent can be dissolved or suspended in appropriate liquids, for example in liquid polyethylene glycols or vegetable oils. Agents with appropriate physical properties are preferably prepared as granules.

The synthetic steps are carried out by known procedures, which are described below in several examples.

EXAMPLE 1

4-[5-(4'-Isopropylphenyl)-3-oxopentyl]benzoic acid methyl ester (a)

4-[5-(4'-isopropylphenyl)-3-oxo-1,4-pentadienyl]benzoic acid methyl ester 94.1 g (0.50 Mol) 4'-isopropylbenzalacetone and 91.8 g (0.56 Mol) 4-formylbenzoic acid methyl ester were dissolved in 500 mL methanol under nitrogen and reacted, with stirring, with 45 mL 2N sodium hydroxide within 5 minutes. After one hour 45 mL 2N sodium hydroxide is added, and stirring continued for an additional three hours. The separated product is removed by suction, washed to neutrality with cold methanol, and recrystallized from 675 mL methanol with addition of 70 mL ethylacetate. Pale yellow crystals, melting point 112–115 C[1] Yield 84.9 g (51%).

$^1$H-NMR-spectrum (CDCl$_3$)[2]: 1.27 d (6): (CH$_3$)$_2$CH; 3.93 m (1): (CH$_3$)$_2$CH; 3.93 s (3): CH$_3$O; 6.80 to 8.2 m (12) aromatic, 4 =CH—.

[1] Melting points were determined with a Kofler-Hotstage-Microscope and were not corrected.
[2] Determined at 60 MHz. The chemical shifts are given in ppm versus TMS (δ=0.0), the relative intensities are added in parentheses. s=singlet, d=doublet, t=triplet, q=quartet, m=multiplet.

(b)

Preparation, according to the invention, of 4-[5-(4'-isopropylhenyl)-3-oxopentyl]benzoic acid methyl ester 33.4 g (0.10 Mol) 4-[5-(4'-isopropylphenyl)-3-oxo-1,4-pentadienyl]benzoic acid methyl ester are dissolved in 40 mL (0.385 Mol) benzylalcohol, reacted with 0.20 g (0.2 Mol) Tris(triphenylphosphin)ruthenium-(II)-chloride under nitrogen, and heated for two hours in an air cooler under a slow stream of nitrogen at 190°–200° C. (bath temperature). Subsequently the benzaldehyde formed, together with the remaining benzylalcohol, is removed under vacuum and, to complete the reduction, the residue is heated for an adidtional two hours at 190°–200° C. (bath temperature) under nitrogen with 30 mL fresh benzylalcohol and 0.15 g catalyst. The volatile components are then removed at 0.1 mbar and 10° C. (bath temperature) and the reddish brown oily residue taken up in dichloromethane. After column chromatographic purification on silica gel with dichloromethane, the solvent is removed in a vacuum and the residue distilled at 0.03 mbar and 225° C. in a spherical tube heater. Colorless oil with refractive index of n$_D^{25}$=1.5445. Yield 11.2 g (33%).

C$_{22}$H$_{26}$O$_3$ (338.4).

Mol.wt.: 338 (determined via mass spectrometry)[x].
[x] with electron pulse ionization (70 eV)

IR-spectrum (film): ν (C=O) 1720, 1710 cm$^{-1}$.

$^1$H-NMR-spectrum (CDCl$_3$): 1.20 s (6): (CH$_3$)$_2$CH; 2.47 to 3.13 m (9): 2 ArCH$_2$CH$_2$ and (CH$_3$)$_2$CH; 3.9 s (3): OCH$_3$; 6.93 to 8.10 m (8): aromatic.

EXAMPLE 2

4-[5-(4'-isopropylphenyl)-3-hydroxypentyl]benzoic acid 34.0 g (0.10 mol) crude 4-[5-(4'-isopropylphenyl)-3-oxopentyl]benzoic acid methyl ester, prepared according to Example 1, are dissolved in 100 mL ethanol and slowly reacted at 0°–10° C. with an ice cold solution of 2.0 g (0.053 Mol) sodium borohydride in 10 mL water. After the addition is complete the coolant is removed and the reaction mixture stirred for 2.5 hours at room temperature. 13 g Potassium hydroxide are then added, stirring is continued for an additional 3 hours at room temperature and the mixed allowed to stand overnight. After dilution of the reaction mixture with water, it is extracted twice with ether, the aqueous phase is acidified with concentrated hydrochloric acid, and the separated product taken up in ethyl acetate. The product is washed with water until neutral, dried over soidum sulfate, and the solvent removed in vacuo. The residue is purified chromatographically, using silica gel and CH$_2$Cl$_2$/CH$_3$OH (95/5). After removal of the solvent it is crystallized from acetonitrile. Colorless crystals, m.p. 104°–106° C. Yield 12.7 g. (39%).

C$_{21}$H$_{26}$O$_3$: (326.4).

mol. wt.: 326 (via mass spectrometry).

IR-spectrum (KBr): ν (OH) 3500 to 2400 cm$^{-1}$; ν (C=C) 1685 cm$^{-1}$.

$^1$H-NMR-spectrum (CDCL$_3$): 1.23 d (6): (CH$_3$)$_2$CH; 1.57 to 2.07 m (4): 2 ArCH$_2$CH$_2$; 2.50 to 3.03 m (5): 2 ArCH$_2$CH$_2$ and (CH$_3$)$_2$CH; 3.67 m (1): CH(OH); 6.67 wide s (2): OH, COOH; 7.03 to 8.13 m (8): aromatic.

EXAMPLE 3

4-[5-(4'-tertbutylphenyl)-3-hydroxypentyl]benzoic acid isopropyl ester 34.0 g (0.10 Mol) 4-[5-(4'-tert.butylphenyl)-3-hydroxypentyl]benzoic acid, prepared analogously to examples 1 and 2 is refluxed for 20 hours in 300 mL isopropanol and 5 mL concentrated sulfuric acid. After cooling, the reaction mixture is poured into ice water and shaken with dichloromethane. The organic phase is washed with water, then with an aqueous sodium bicarbonate solution, and finally washed to neutrality with water. After drying over sodium sulfate, the solvent is removed in vacuo and the colorless residue purified chromatographically on silica gel with CH$_2$Cl$_2$/CH$_3$OH (98/2). After removal of the solvent in vacuo, the product is crystallized from petroleum ether (40°–60° C. fraction). Colorless crystals, m.p. 47°–48° C., yield 18.4 g. (48%).

C$_{25}$H$_{34}$O$_3$ (382.5).

Mol. wt.: 382 (via mass spectrometry).

IR-spectrum (KBr) ν(OH) 3600 to 2800 cm$^{-1}$; ν (C=O) 1720 cm$^{-1}$.

| $^1$H—NMR-spectrum (CDCl$_3$): | |
| --- | --- |
| 1.30 s  ⎫ | (CH$_3$)$_3$C |
| 1.33 d  ⎬ (15) | (CH$_3$)$_2$CHO |
| 1.53 to 2.07 m (5) | 2ArCH$_2$CH$_2$ and OH (exchangeable with D$_2$O) |
| 2.50 to 3.00 m (4) | 2ArCH$_2$CH$_2$ |
| 3.60 m (1) | CH(OH) |
| 5.23 m (1) | (CH$_3$)$_2$CHO |
| 6.53 to 8.10 m (8) | aromatic |

EXAMPLE 4

N-Carboxymethyl-4-[5-(4'-tert.butylphenyl)-3-hydroxypentyl]benzamid (a)

4-[5-(4'-tert.butylphenyl)-3-acetoxypentyl]benzoic acid 34.0 g (0.10 Mol) 4-[5-(4'-tert.butylphenyl)-3-hydroxypentyl]benzoic acid and 0.30 g (2.2 mMol) anhydrous zinc chloride are suspended in 50 mL glacial acetic acid and reacted with 14.3 mL (0.20 Mol) acetylchloride, resulting in a clear solution. After stirring at room temperature for two hours the reaction mixture is poured into ice water. The separated product is taken up in chloroform and washed with water. After drying over sodium sulfate the solvent is removed in vacuo and the colorless crystallizable crude product used for further reactions without purification. Crude yield 38.3 g (100%).

| $^1$H—NMR-spectrum (CDCl$_3$): | |
|---|---|
| 1.30 s (9) | (CH$_3$)$_3$C |
| 1.63 to 2.13 m | 2 ArCH$_2$CH$_2$ and |
| 2.0 s | CH$_3$CO |
| 2.37 to 2.90 m (4) | 2 ArCH$_2$CH$_2$ |
| 4.97 m (1) | CH(OCOCH$_3$) |
| 6.83 to 8.10 m (8) | aromatic |
| 11.83 wide s (1) | COOH |

(b)

Preparation, according to the invention, of N-carboxymethyl-4-[5-(4'-tert.butylphenyl)-3-hydroxypentyl]benzamid 38.3 g (0.10 Mol) crude 4-[5-(4-'tert.butylphenyl)-3-acetoxypentyl]benzoic acid and 12 mL (0.165 Mol) thionylchloride in 200 mL toluene are heated under reflux for 3.5 hours. Solvent and excess thionylchloride are distilled off under vacuum and the oily residue taken up in 250 mL dry dioxane. This solution is added dropwise with vigorous stirring at 5° to 7° C. to a solution of 29.6 g (0.30 Mol) glycine and 15.6 g (0.39 Mol) sodium hydroxide in 350 mL water, stirred three hours at room temperature and left to stand overnight. 20 g sodium hydroxide are then added and stirred an additional 3.5 hours at room temperature. Finally the reaction mixture is diluted with water and, after acidification with concentrated hydrochloric acid, the precipitated end product is taken up in ethyl acetate. After two washings the organic phase is dried over sodium sulfate, the solvent removed in vacuo and the residue crystallized from acetonitrile. Colorless crystals, m.p. 133°–135° C.; yield 32.2 g (81%).

C$_{24}$H$_{31}$NO$_4$: (397.5).

Mol. wt. 397 (via mass spectrometry).

IR-spectrum (KBr): $\nu$ (OH) 3600 to 2400 cm$^{-1}$; $\nu$ (C=O) 1725 cm$^{-1}$; $\nu$ (NH) 3360 cm$^{-1}$.

$^1$H-NMR-spectrum (d$_6$-acetone): 1.23 s (9); (CH$_3$)$_3$C; 1.57 to 2.03 m (4): 2 ArCH$_2$C$\underline{H}_2$; 2.50 to 3.03 m (4): 2 ArC$\underline{H}_2$CH$_2$; 3.60 m (1): C$\underline{H}$(OH); 4.10 to 4.20 2 s (2): NCH$_2$; 6.47 to 8.17 m (11): aromatic, NH, OH, COOH.

Further compounds of general formula 1 were prepared by methods analogous to those described in the examples and are listed, together with their melting points, in the following table.

TABLE 2

R$^1$—⟨aryl⟩—CH$_2$CH$_2$—X—CH$_2$CH$_2$—⟨aryl⟩—CO—R$^2$

| No. | R$^1$ | X | R$^2$ | m.p. (°C.)$^{(x)}$ | Solvent$^{(xx)}$ |
|---|---|---|---|---|---|
| 1 | H | CO | OH | 140–141 | (a) |
| 2 | (CH$_3$)$_2$CH | CO | OCH$_3$ | n$_D^{25}$ = 1.5445 (oil)$^{(xxx)}$ | |
| 3 | (CH$_3$)$_3$C | CO | OH | 139–140 | (f) |
| 4 | (CH$_3$)$_3$C | CO | OCH$_3$ | 47–48 | (d) |
| 5 | H | CHOH | OH | 99–100 | (a) |
| 6 | H | CHOH | OCH$_2$CH$_2$CH$_3$ | 48–49 | (b) |
| 7 | (CH$_3$)$_2$CH | CHOH | OH | 104–106 | (a) |
| 8 | (CH$_3$)$_2$CH | CHOH | OCH$_2$CH=CH$_2$ | 55–56 | (d) |
| 9 | (CH$_3$)$_3$C | CHOH | OH | 122–123 | (a) |
| 10 | (CH$_3$)$_3$C | CHOH | OCH$_2$CH$_3$ | 46–47 | (d) |
| 11 | (CH$_3$)$_3$C | CHOH | OCH(CH$_3$)$_2$ | 47–48 | (d) |
| 12 | H | CO | NHCH$_2$COOH | 126–128 | (a) |
| 13 | H | CHOH | NHCH$_2$COOH | 97–99 | (c) |
| 14 | (CH$_3$)$_2$CH | CHOH | NHCH$_2$COOH | 116–119 | (e) |
| 15 | (CH$_3$)$_3$C | CHOH | NHCH$_2$COOH | 133–135 | (a) |

$^{(x)}$Melting points were obtained with a Kofler-Hotstage-Microscope and are not corrected
$^{(xx)}$crystallized from:
(a) acetonitrile
(b) 1-chlorobutane/petroleum ether (40–60)
(c) ethylacetate/diisopropylether
(d) petroleum ether (40–60)
(e) acetonitrile/chloroform
(f) 1-chlorobutane
$^{(xxx)}$boiling point 225° C./0.03 mbar

EXAMPLE 5

4-[5-(4'-isopropylphenyl)-3-oxopentyl]benzoic acid methylester containing pharmaceutical preparation 400 g 4-[5-(4'-isopropylphenyl)-3-oxopentyl]benzoic acid methyl ester are mixed with 200 g polyethylene glycol, and according to the procedure of Scherer, filled into one thousand soft gelatin capsules, each containing 400 mg active.

EXAMPLE 6

4-[5-(4'-tert.butylphenyl)-3-hydroxypentyl]benzoic acid containing pharmaceutical preparation 500 g 4-[5-(4'-tert.butylphenyl)-3-hydroxypentyl]benzoic acid are finely pulverized and then mixed with talc and calcium stearate; after thorough mixing they are filled into two thousand hard gelatin capsules, so that each capsule contains 250 mg active.

While the invention has been decribed in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. Compound comprising benzoic acid derivatives of formula (1)

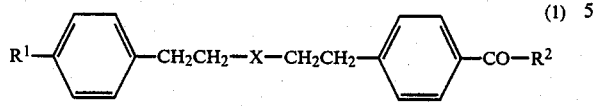

and their physiologically compatible salts, where
R¹=H, isopropyl, or t-butyl
X=

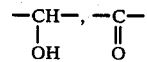

and
R²=—OH, or —OR', where R¹ may be a straight chain, branched, saturated or unsaturated $C_1$ to $C_3$-alkylmoiety, or a —NHCH₂COOH— group.

2. A pharmaceutical composition comprising a compound according to claim 1, in a pharmaceutically acceptable solvent or carrier.